(12) United States Patent
Sula et al.

(10) Patent No.: US 7,519,416 B2
(45) Date of Patent: Apr. 14, 2009

(54) DIAGNOSTIC METHOD UTILIZING STANDARD LEAD ECG SIGNALS

(75) Inventors: Anatoli Sula, Moscow (RU); Vladimir Grishin, Cleveland, OH (US); Youri Kitachine, Moscow (RU); Mikhail Reva, Moscow (RU)

(73) Assignee: Heartview, LLC, Cleveland, OH (US)

( * ) Notice: Subject to any disclaimer, the term of this patent is extended or adjusted under 35 U.S.C. 154(b) by 519 days.

(21) Appl. No.: 11/048,979

(22) Filed: Feb. 2, 2005

(65) Prior Publication Data

US 2005/0192503 A1    Sep. 1, 2005

Related U.S. Application Data

(63) Continuation-in-part of application No. 10/358,419, filed on Feb. 4, 2003, now abandoned.

(60) Provisional application No. 60/353,336, filed on Feb. 4, 2002.

(51) Int. Cl.
*A61B 5/402* (2006.01)
(52) U.S. Cl. .................................. 600/509
(58) Field of Classification Search ........ 600/382, 600/509; 607/4, 5, 9, 115
See application file for complete search history.

(56) References Cited

U.S. PATENT DOCUMENTS

| 5,058,598 | A  | * | 10/1991 | Nicklas et al. ............ 600/512 |
| 5,331,960 | A  | * | 7/1994  | Krenzke .................... 600/382 |
| 6,496,720 | B1 |   | 12/2002 | Field |
| 6,694,178 | B1 |   | 2/2004  | Soula et al. |
| 7,092,748 | B2 | * | 8/2006  | Valdes Sosa et al. ....... 600/407 |
| 7,245,962 | B2 | * | 7/2007  | Ciaccio et al. ............. 600/512 |
| 2003/0167013 | A1 |   | 9/2003 | Anatoly et al. |

* cited by examiner

*Primary Examiner*—Carl H Layno
*Assistant Examiner*—Frances P Oropeza
(74) *Attorney, Agent, or Firm*—Fay Sharpe LLP

(57) ABSTRACT

A new and superior strategy for analyzing electrocardiograms (ECG) is disclosed. The strategy utilizes standard leads obtained from only limb electrodes from a conventional electrocardiography system. The strategy determines new additional leads which are utilized in a new calculation of values which upon appropriate analysis, provide new information as to electrical fluctuations in the heart. Also disclosed are processes for mapping and transposing the values in digital form and optionally upon a three-dimensional heart model. And, related systems and computer-readable media are disclosed for performing these processes.

1 Claim, 16 Drawing Sheets

$\lambda = R1/(R1+R2)$
$\lambda = 0 \Rightarrow \alpha = 0 \Rightarrow I$
$\lambda = 0.5 \Rightarrow \alpha = -30 \Rightarrow aVL$
$\lambda = 1.0 \Rightarrow \alpha = -60 \Rightarrow -III$ t1 t2 t3

DIAGNOSTIC METHOD UTILIZING STANDARD LEAD ECG SIGNALS

CROSS REFERENCES TO RELATED APPLICATIONS

This is a continuation-in-part application of U.S. application Ser. No. 10/358,419 filed on Feb. 4, 2003 now abandoned which claims priority from U.S. provisional application Ser. No. 60/353,336 filed on Feb. 4, 2002.

FIELD OF THE INVENTION

The present invention relates to electrocardiography (ECG) analysis.

BACKGROUND

ECG was first used in the beginning of the twentieth century. Over the last several decades, a variety of diagnostic procedures have been developed for sensing and analyzing activity of the human heart. These include electrocardiography, vectorcardiography and polarcardiography, all of which depend upon related instrumentation used to produce records derived from voltages produced by the heart on the surface of the human body.

The records so produced are graphical in character and require interpretation and analysis to relate the resulting information to the heart condition of the patient or other subject. Historically, such records have been produced directly as visible graphic recordings from wired connections extending from the subject to the recording device. With advances in computer technology, it has become possible to produce such records in the form of digitally stored information for later replication or retrieval and analysis. Likewise, with advances in communication technology, remote or wireless sensing has become possible.

The production of a conventional 12 lead electrocardiogram (also sometimes referred to as an ECG) involves the placement of 10 lead electrodes (one of which is a ground or reference electrode) at selected points on the surface of a subject's body. Each electrode acts in combination with one or more other electrodes to detect voltages produced by depolarization and repolarization of individual heart muscle cells. The detected voltages are combined and processed to produce 12 tracings or "leads" of time varying voltages. The leads so produced are as follows:

| Lead | Voltage |
| --- | --- |
| I | vL − vR |
| II | vF − vR |
| III | vF − vL |
| aVR | vR − (vL + vF)/2 |
| aVL | vL − (vR + vF)/2 |
| aVF | vF − (vL + vR)/2 |
| V1 | v1 − (vR + vL + vF)/3 |
| V2 | v2 − (vR + vL + vF)/3 |
| V3 | v3 − (vR + vL + vF)/3 |
| V4 | v4 − (vR + vL + vF)/3 |
| V5 | v5 − (vR + vL + vF)/3 |
| V6 | v6 − (vR + vL + vF)/3 |

In this standard, which is the most widely used system for making short term electrocardiographic recordings of supine subjects, the potentials indicated above, and their associated electrode positions, are as follows:

vL potential of an electrode on the left arm;
vR potential of an electrode on the right arm;
vF potential of an electrode on the left leg;
v1 potential of an electrode on the front chest, right of sternum in the $4^{th}$ rib interspace;
v2 potential of an electrode on the front chest, left of sternum in the $4^{th}$ rib interspace;
v4 potential of an electrode at the left mid-clavicular line in the $5^{th}$ rib interspace;
v3 potential of an electrode midway between the v2 and v4 electrodes;
v6 potential of an electrode at the left mid-axillary line in the $5^{th}$ rib interspace;
v5 potential of an electrode midway between the v4 and v6 electrodes; and
vG (not indicated above) is a ground or reference potential with respect to which potentials vL, vR, vF, and v1 through v6 are measured. Typically, though not necessarily, the ground or reference electrode is positioned on the right leg. As is apparent from the foregoing, a 12 lead system uses 10 electrodes on a patient's body.

Six lead electrocardiograms are also known. These systems do not use any chest electrodes and so, only utilize electrodes placed on the left and right arms, and left and right legs. Accordingly, these systems use a total of 4 electrodes on a patient's body.

Correct interpretation of an ECG requires a great deal of experience since it involves familiarity with a wide range of patterns in the various leads. Any ECG which uses an unconventional system of leads necessarily detracts from the body of experience that has been developed in the interpretations of conventional ECGs, and may therefore be considered generally undesirable. The leads generated would be understandable only by a relative few who were familiar with the unconventional system. Despite its widespread use, clinicians acknowledge that modern ECG analysis suffers from insufficient sensitivity and specificity.

Because of the disadvantages of regular ECG methods and despite a common opinion that all fruitful information from ECG has already been determined by analysis of standard PQRST wave properties, the present inventors developed a method which surpasses regular ECG analysis. That development is the subject U.S. Pat. No. 6,694,178, herein incorporated by reference. A description of the PQRST complex is provided in the '178 patent. The '178 patent describes a method of conversion of one ECG lead to produce a three-dimensional artificial topological model. The topological information of this model enables the extraction of useful information from low amplitude fluctuations of the initial signal. This information is simply unavailable from traditional methods of ECG analysis, as these methods consider most fluctuations, as noise.

However, this method of ECG analysis according to the '178 patent has two principle limitations. First, not all pathological states of a heart appear in one lead. For example, small focal (transmural) myocardial infarctions are, in many instances, impossible to reveal from one lead. Secondly, using only one lead in a number of cases, causes various diseases having similar topological images, to be indiscernible from one another. Specifically, the information associated with one lead is insufficient for identifying excitation direction and sharing of changes on the left and right atriums, and left and right ventricles. Therefore, the method of the '178 patent is effective only for detection of certain deviations, but is ineffective for derivation of diseases, in which the exact definition of the type of deviation and its localization must be determined.

To overcome these disadvantages, the present inventors proceeded from the analysis of fluctuations of one lead, i.e. analysis of electrical potentials at one point on the surface of a patient's body, to analyze the fluctuations of electrical potentials at several surface points on a body. This strategy is the subject of DE 199 33 277 A1. This strategy enables the construction of a topological model with 12 standard ECG leads. The topological model of a heart in this strategy provides different color patterns for different diseases, and so, allows an effective diagnosis of disease type. However, the topological heart model of a patient constructed by this strategy has a strictly discrete structure because the field of electrical fluctuations on the surface of the patient's body is determined from only a relatively small number of surface points. As a result, surface points, which are not laying on lines of standard ECG leads, do not participate in forming the topological model. Therefore, when surface potentials are constant at the points (i.e. locations of the 10 electrodes) of the standard 12 lead system, but changes occur at other points, the topological model does not show these changes. Electrical fluctuations occurring at regions besides the locations of the electrodes in a 12 lead system can be very important for early detection of many pathologies. For example, there is a wide group of clinically important hidden cases of ischemic disease (a decrease in blood supply), which are not revealed by a standard 12 lead system of a resting ECG but which may be indicated by detection at other points. Therefore, the approach described in DE 199 33 277 A1 is unable, or at least severely deficient, in identifying such conditions, thus leading to unexpected clinical consequences.

The present discovery described herein provides a dramatic improvement in ECG analysis in comparison to currently known ECG analysis available today.

SUMMARY OF THE INVENTION

In a first aspect, the present invention provides a method for assessing the state of a heart. The method comprises placing limb electrodes on a body of a patient for which assessment of the state of the heart is to be made. The method further comprises selecting two standard leads from the limb electrodes. The method also comprises measuring electrical voltages in each selected standard lead to thereby define two arrays of base voltages. The method further comprises selecting a time interval. The method comprises calculating additional leads from the arrays of base voltages defined and the time interval selected. And, the method comprises reviewing the calculated additional leads to thereby assess the state of the heart of the patient.

In another aspect according to the present invention, a system for assessing the state of a heart is provided. The system comprises a processor including (i) inputs to receive signals from two standard leads selected from limb electrodes, (ii) a storage device for storing information, and (iii) at least one output. The processor is configured to (a) calculate additional leads from the signals from the two standard leads, (b) store information relating to the calculated additional leads in the storage device, and (c) selectively provide the stored information at the at least one output. The system also comprises a display device in communication with the at least one output and configured to display the stored information related to the calculated additional leads. Display of the stored information enables assessment of the state of the heart.

In a further aspect provided by the present invention, a computer-readable medium is provided. The computer-readable medium has computer executable instructions for performing a method of assessing the state of a heart using limb electrodes. The method comprises defining two arrays of base voltages from two standard leads determined from the limb electrodes. The method also comprises calculating additional leads from the arrays of base voltages defined and a selected time interval. The additional leads enable the assessment of the state of the heart.

BRIEF DESCRIPTION OF THE DRAWINGS

The present invention may be better understood, and further advantages and uses thereof more apparent, when considered in view of the following detailed description of preferred embodiments, taken with the accompanying drawings in which.

DETAILED DESCRIPTION OF THE PREFERRED EMBODIMENTS

Figure 1:
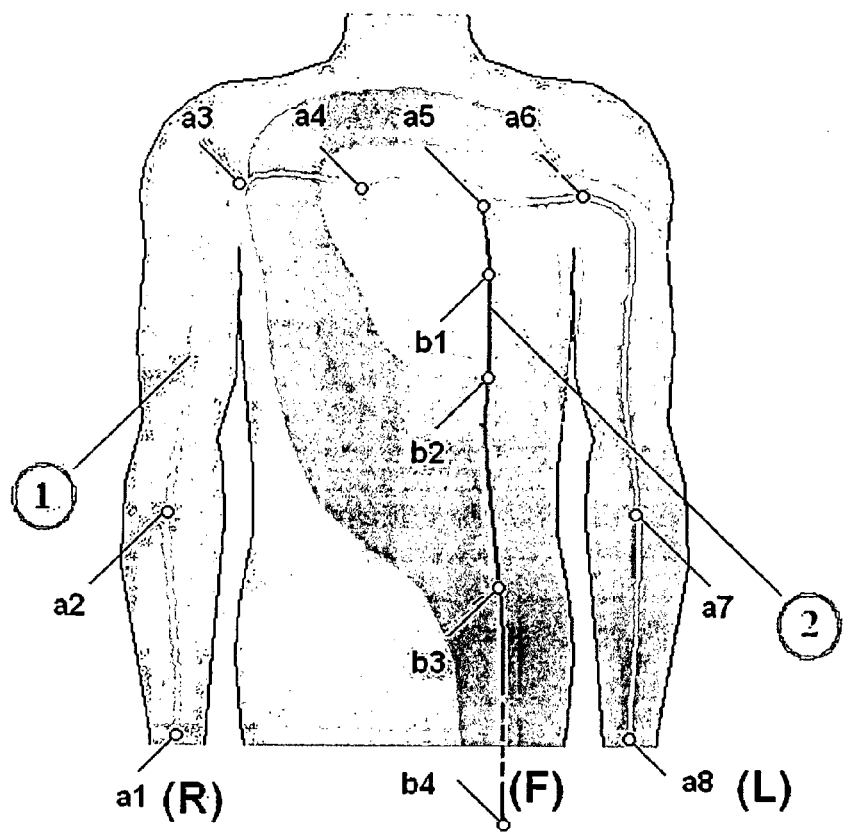
FIG. 1 is an approximate map of surface potentials along a human body at the moment of maximum depolarization.

The present invention provides a new and unique strategy for ECG analysis based upon only 4 electrodes placed on a subject's body. The 4 electrodes are placed on the arms and legs of a subject, and correspond to the limb electrodes used in a 6 lead system or a 12 lead system. The invention enables the construction of highly sensitive three-dimensional anatomic maps of a heart on a display screen with standard ECG leads. The constructed model can utilize a discoloration of an epicardium on the map to indicate not only the existence of a pathological state, but also indicate the location of centers of change of a myocardium at the earliest stages of a pathological state. The present invention also provides systems and computer-readable media for performing the noted strategies.

The present invention utilizes electrical voltages or signals of new leads, referred to herein as "additional leads." The voltages or signals of additional leads can be obtained at any moment by registration of ECG electrical voltages of any two standard leads, for example I and III from a standard 12 lead system. The signals of additional leads provide new diagnostic information about the values and localizations of pathological changes. The signals of the additional leads are characterized by high repeatability, and also high sensitivity and specificity.

The present invention utilizes only limb electrodes, such as a first electrode placed on a patient's left arm, a second electrode placed on a patient's right arm, a third electrode placed on a patient's left leg, and a fourth electrode designated as ground, and which optionally can be placed on a patient's right leg. Preferably, the limb electrodes placed on arms are actually positioned on the patient's wrists. And, preferably, the limb electrodes placed on legs, are actually positioned on the patient's ankles. As described in greater detail herein, standard leads are determined from these limb electrodes in accordance with the determination of leads in a 6 lead or 12 lead system. In accordance with a significant feature of the present invention, upon selection of any two of the standard leads determined from the limb electrodes, the selected leads are processed as described herein to provide unique and valuable information relating to the patient's heart.

As described in greater detail herein, an analog electrical circuit is provided which is derived from a new model of occurrence of electrical voltages in standard limb leads. The new model is based on the registration of electromagnetic radiation of a myocardium, which previously, has not been surveyed. The analog electrical circuit allows at any instant the determination of a large number, for example 180, of additional leads based upon only a PQRST-complex, and two entry voltages from any standard limb leads (for example, I and III). If using digital ECG, the additional leads for each instant can be calculated by a microprocessor at each moment by analog-to-digital (AD) conversion in real time. For example, at a frequency of AD-conversion of 500 Hz, 90,000 digital values can be determined for a 1 second interval.

The thus obtained digital arrays of a large number of additional leads are highly sensitive indicators of any metabolic changes of cells of a myocardium. Even in short-term episodes of hypoxia, otherwise undetectable by use of standard ECG, the arrays of additional leads indicate discernible changes in the myocardium. This provides a significant advantage to the investigator or physician.

The character of change of the digital arrays of additional leads depends not only on the value of changes in a myocardium, but also upon the location of the center of changes.

For efficiency and simplicity of observation of such large digital arrays, the obtained values of signals of additional leads can be encoded by color and transposed on a surface of a computerized anatomic three-dimensional map of a heart according to the calculated location.

Upon transposing the additional leads upon the anatomic heart model, a fluctuation field can immediately show locations and degree of deviations. In a preferred aspect of the invention, each type of pathology has a specific color relief and accordingly, an appropriate heart portrait is produced. The present invention enables a more precise method to distinguish the different pathologies or their combinations. The fluctuation field varies much earlier, as compared to deviations associated with a standard ECG. Accordingly, the present invention provides a dramatic increase in both sensitivity and specificity of the diagnosis, and further enables a dramatic increase in early detection and identification of a pathological state and its development, particularly for conditions that are undetectable by standard ECG strategies.

Figure 2:
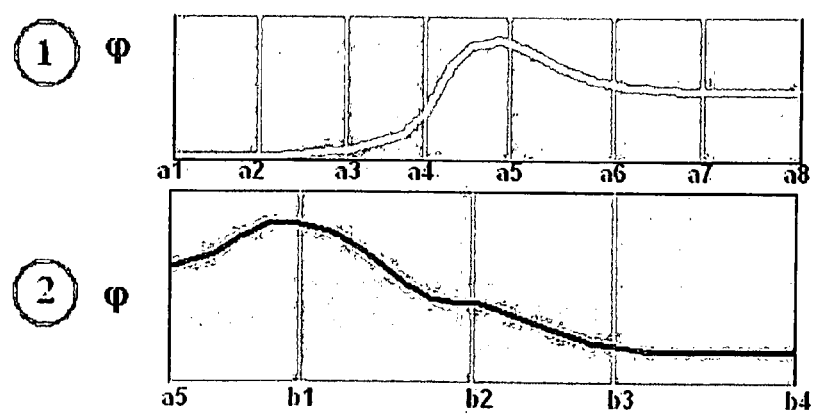
FIG. 2 is a graph of the change in electrical potential along the locations designated in FIG. 1.

A preferred embodiment method according to the present invention for defining potentials of additional leads is as follows. Referring to FIG. 1, if the negative terminal of the measuring instrument connects to a point R (right arm), an approximation of equipotential curves (lines of an identical potential) will correspond to the pattern represented in FIG. 1 for the normal orientation of a heart's electrical axis. If measuring electrical potential along lines a1-a8 (line 1) and a5, b1-b4 (line 2), the change of potential along these lines will have a similar appearance as the graphs 1 and 2 in FIG. 2. The regions a1-a3, a6-a8 and b3-b4 have practically constant potentials, in that these regions are passive conductors for electric current. At the same time, regions a4-a6 and a5-b2 have sources of electrical current. From the theory of electrical circuits, it is known that a potential diagram can be constructed which corresponds to any connection of passive units and sources of electrical current.

Figure 3:
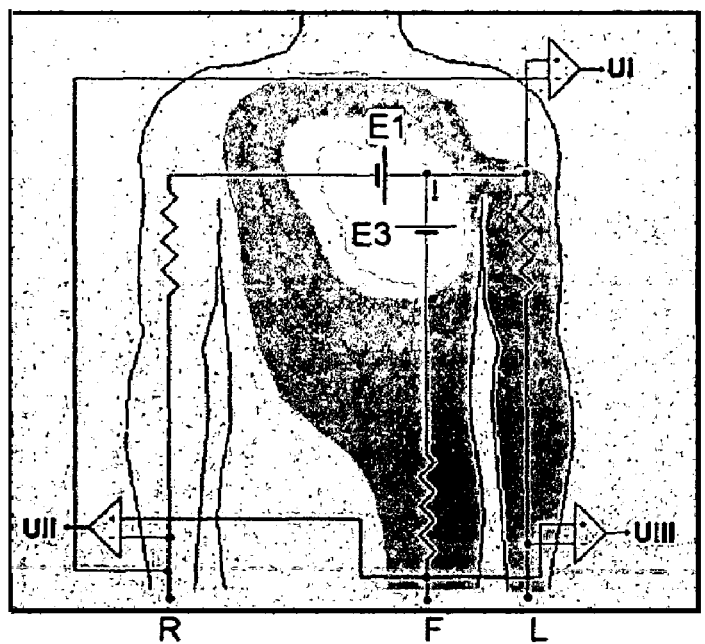
FIG. 3 is an analog electrical circuit corresponding to the map of body surface potentials in FIG. 1, the circuit illustrating standard leads I, II, and III.
Figure 4:
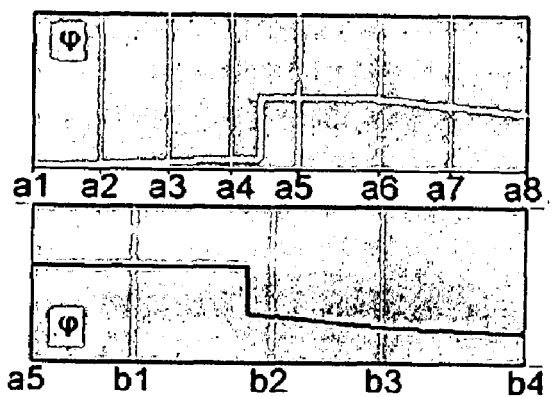
FIG. 4 is a graph of the change in electrical potential along the locations designated in FIG. 1, however, according to the circuit of FIG. 3.
Figure 5:
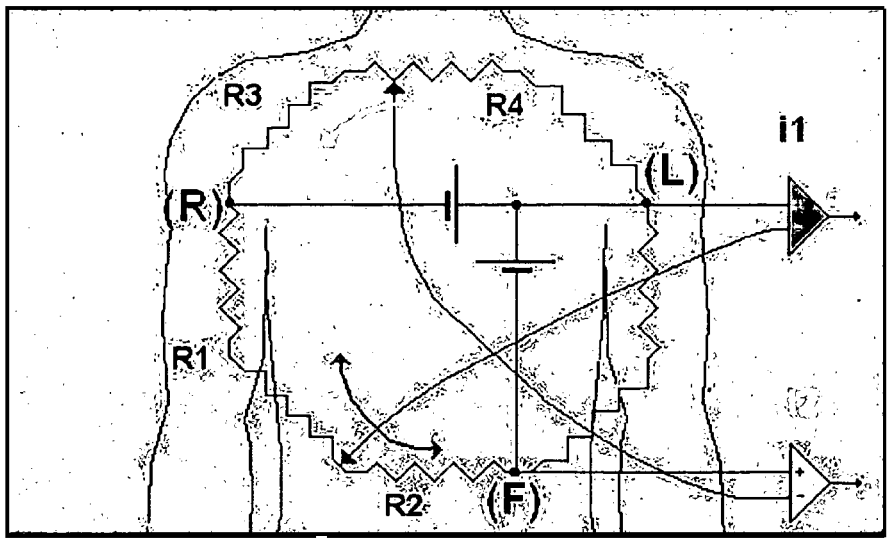
FIG. 5 is a modified analog electrical circuit corresponding to the map of body surface potentials.

A simplified model of the real potential diagrams of FIG. 1 is represented in FIG. 3. FIG. 4 is a graph of the change in electrical potential along the locations noted in FIG. 1, however according to the circuit in FIG. 3. This circuit depicted in FIG. 3 contains two current sources E1, E3, and three resistors. The resistors characterize conductivity of a human body between E1, E3 and points of connections of devices, which measure electrical potentials in leads I, II and III. The voltage U1 of lead I is closed to the electromotive force (EMF) of the source E1, and U3 of lead III is closed to the EMF of the source E3. Because practically there is no voltage drop along resistors, this circuit for measurement of terminal potentials can be modified as shown in FIG. 5. The modified circuit can be considered a ring conductor passing through points of 3 standard leads I, II, III, and two EMF sources inside this ring.

Referring further to FIG. 5, the device I1 has a positive terminal connected to a point L, and a negative terminal that moves along resistors between points R and F. When the negative terminal is moved to a point R, the instrument I1 measures lead I. When the negative terminal is moved to a point F, the instrument measures lead-U3. When the negative terminal is located in the middle between R and F (and specifically, equally between R1 and R2), the negative terminal measures lead aVL. If the negative terminal of the device is at any intermediate point between R and F, a new lead in a six-axial coordinate system between leads I and III, as shown in FIG. 6 gray sector, is obtained.

Figure 6:
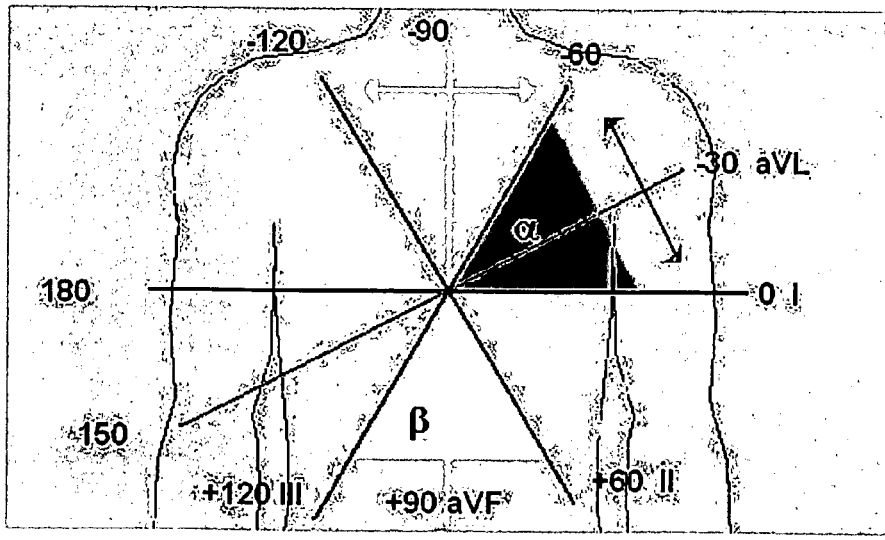
FIG. 6 illustrates a six axes coordinate system and relationship between several standard leads.

Referring to FIG. 6, consider the parameter λ=R1/(R1+R2), where R1 and R2 are resistances between the current position of the negative terminal of the device and points R and L. At change of a position of λ a the negative terminal of the device varies from zero (0) at a point R to one (1) at a point F. Accordingly, an angle in the standard cardiac six axes coordinate system varies from a minus 60 up to 0. Thus, the value λ=0.5 corresponds to a reinforced lead aVL, as specifically shown in FIG. 6.

Figure 7:
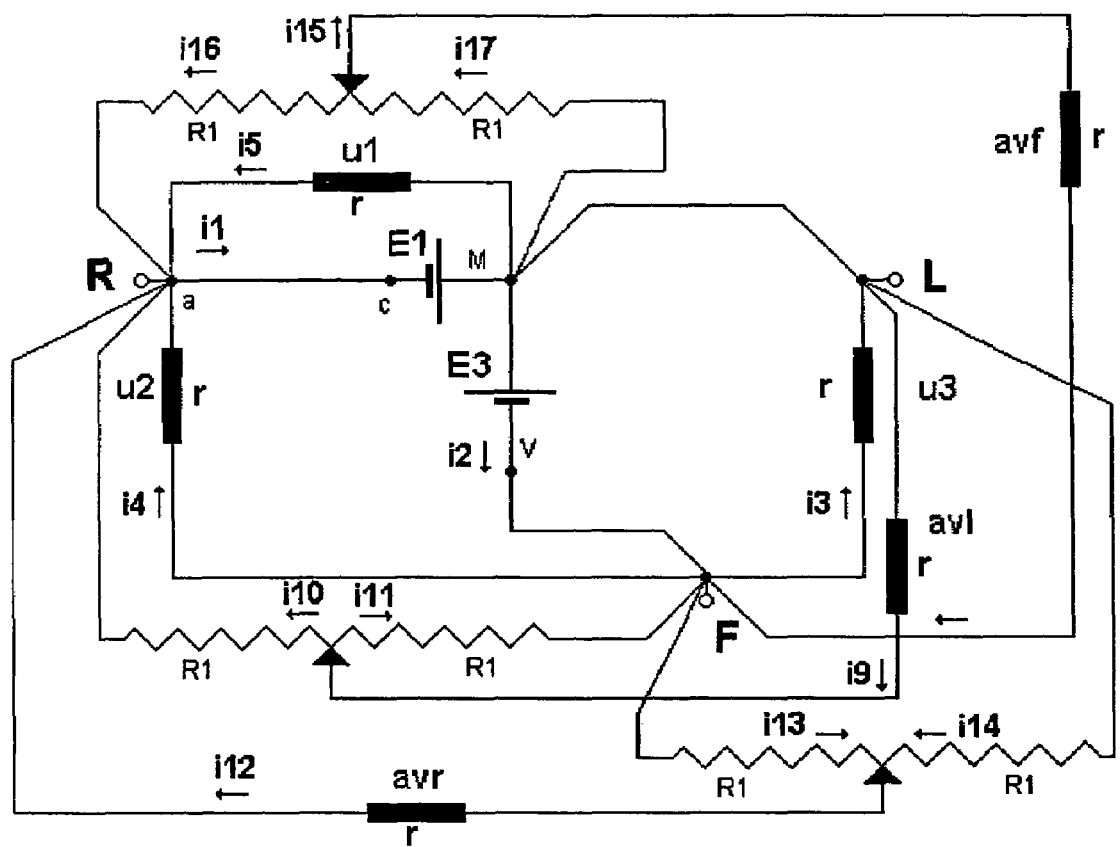
FIG. 7 is an equivalent circuit illustrating measurement of additional leads, according to a preferred embodiment of the present invention.

A similar correspondence exists for sectors bound with leads aVF and aVR. For aVF this correspondence is also depicted in FIG. 6. In total, a circuit is obtained as shown in FIG. 7. In this circuit, the value r is an input resistance of the measuring instrument, and R1 is part of the ring conductor. For certainty, the "slipping" contact on FIG. 7 is placed in a middle position corresponding to leads aVR, aVL, aVF.

Moving slipping contacts on to a ring conductor, it is possible at any instant "t" to receive a voltage for any angle a in the standard cardiac six axes coordinate system. The thus obtained electrical voltage for each value of an angle essentially corresponds to an additional lead described herein. The number of additional leads is specified by the number of possible values of an angle a. For practical usage of additional leads, it is expedient to change an angle a through 1 degree, thereby resulting in 180 additional leads. The augmentation of the number of such leads more than 180 is inexpedient, since at smaller increments of change a, the accuracy of the diagnostic data is not significantly increased. The practical implementation of the equivalent circuit represented in FIG. 7, causes difficulties, since for satisfactory results the slipping contacts should make a complete turn in time in about 2 msec thereby corresponding to a frequency of AD conversion of about 500 Hz. To overcome these difficulties, it is expedient to construct a digital algorithm of calculation of additional voltages, which is a discrete model of the analog circuit represented in FIG. 7, and which is readily configured in any microprocessor.

Using Kirchgoff's laws after complex calculations of nodes and circuits, the following relations are obtained.

If α=−60 ... 0, then $$\lambda=(\alpha+60)/60 \qquad (f1)$$

$$\text{Ampl}(\alpha, t)=U1(t)-(1-\lambda)*(U1(t)+U3(t)); \qquad (f2)$$

If α=0 ... +60, $$\lambda=\alpha/60 \qquad (f3)$$

$$\text{Ampl}(\alpha, t)=U1(t)+\lambda*U3(t); \qquad (f4)$$

If α=+60 ... +λ20, $$\lambda=(\alpha-60)/60 \qquad (f5)$$

$$\text{Ampl}(\alpha, t)=U3(t)+(1-\lambda)*U1(t); \text{ (* designates an operation of multiplying).} \qquad (f6)$$

The calculation is performed on three sectors by 60 degrees. Input data are the voltages U1, U3 and parameter λ. It is possible to obtain values U1, U3 at measurement of any combination of two leads from three standard leads, such as I, II, III. If leads I and III are measured,

U1=I, U3=III.

If leads I and II are measured,

U1=I, U3=II-I.

If leads II and III are measured,

U1=II-III, U3=III.

Thus, at any moment of time, measuring voltages in only two limb leads, i.e. I and III, or I and II, or II and III, it is possible to obtain the extended field of signals for all intermediate angles of the six axes coordinate system. The relations for six standard terminal leads can be obtained at values of an angle 0 (I), +60 (II), +120 (III), +30 (aVR), −30 (aVL), +90 (aVF):

$$I=\text{Ampl}(0, t)=U1(t) \qquad (f7)$$

$$II=\text{Ampl}(+60, t)=U1(t)+U3(t) \qquad (f8)$$

$$III=\text{Ampl}(+120, t)=U3(t) \qquad (f9)$$

$$aVL=\text{Ampl}(-30, t)=U1(t)/2-U3(t)/2=(I-III)/2 \qquad (f10)$$

$$aVR=\text{Ampl}(+30, t)=U1(t)+U3(t)/2=(I+II)/2 \qquad (f11)$$

$$aVF=\text{Ampl}(+90, t)=U3(t)+U1(t)/2=(II+III)/2 \qquad (f12)$$

These relations are identical to what are utilized in conventional ECG-devices. That is, these relations correspond to the values resulting from a vector dipole interpretation of average vector QRS generally accepted in the field of heart electrophysiology. However, in comparing vector model values of potential differences, "intermediate" points change since angles are not matched to reinforced leads. Using the strategy according to the present invention; a mismatch of 0.87 between a projection of an average vector QRS on a 30 degrees turned axis and the true value of a signal on this axis, does not occur.

Figure 8:
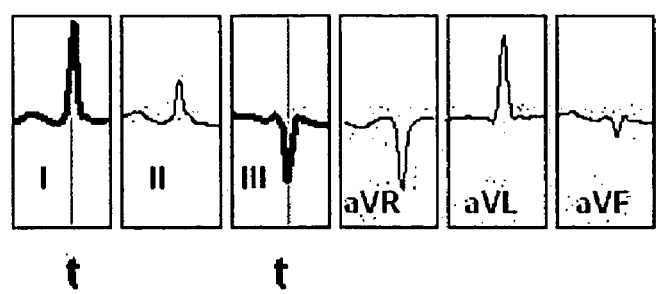
FIG. 8 illustrates representative voltages of several standard leads.
Figure 9:
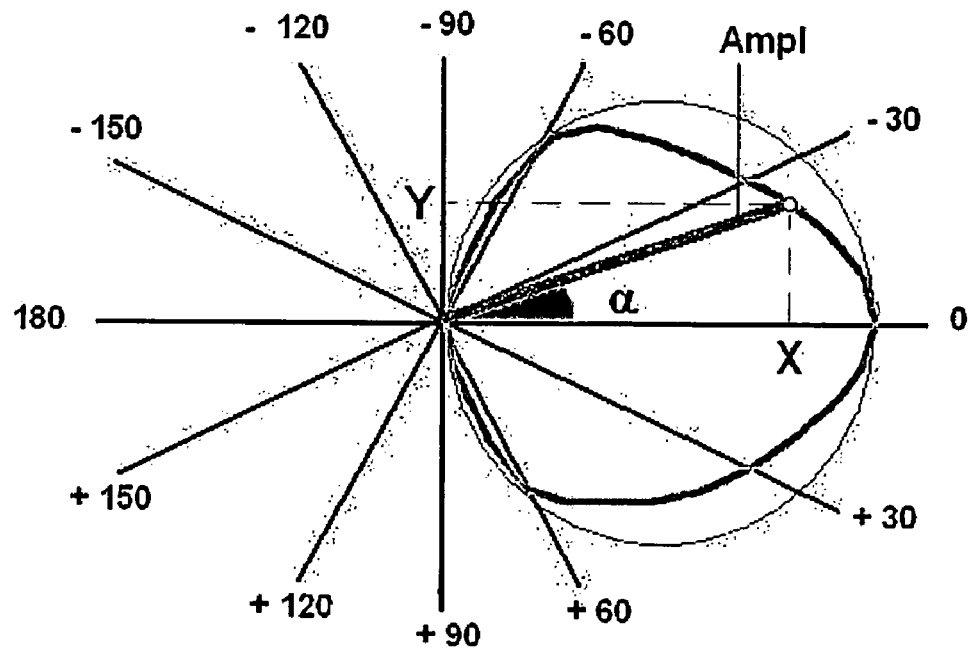
FIG. 9 is a diagram of various voltages in a six axes coordinate system.

The process of the calculation is graphically represented in FIGS. 8 and 9. At first, for each value of an angle α under the formulas set forth above, the value of Ampl (α) is determined. Further, for the value Ampl (α), coordinates X, Y in a rectangular coordinate system are calculated with the formulas:

$$X=\text{Ampl}(\alpha)*\cos(\alpha),$$

$$Y=\text{Ampl}(\alpha)*\sin(\alpha) \text{ (* designates an operation of multiplying).}$$

A curve of change in voltage amplitude for any angle of a coordinate system is shown in FIG. 9. The resulting line can differ from an ideal circle corresponding to a dipole model of electrical excitation of heart. The more pathological deviation, the greater the difference of the ellipse QRS from a circle.

In summary, in each instant it is possible to obtain not only measurements from points corresponding to the terminal leads, but also measurements along a line having, for example, 180 points (in this case one point corresponds to one degree of a coordinate system). Thus, using only two standard leads, such as leads I and III, it is possible to obtain the entire extension of the initial digital array of measurements. These extended arrays allow a detailed analysis of "QRS ellipse" changes over time.

Instead of an "average angle QRS" now it is possible to define in each instant "an instant angle (axis) QRS". The instant axis QRS corresponds to an angle α, at which Ampl (α) achieves some maximum value. Thus all points, which are to the left of an instant axis QRS, correlate with changes in a left ventricle, and the points to the right of an axis QRS correlate with changes in a right ventricle.

Figure 10:
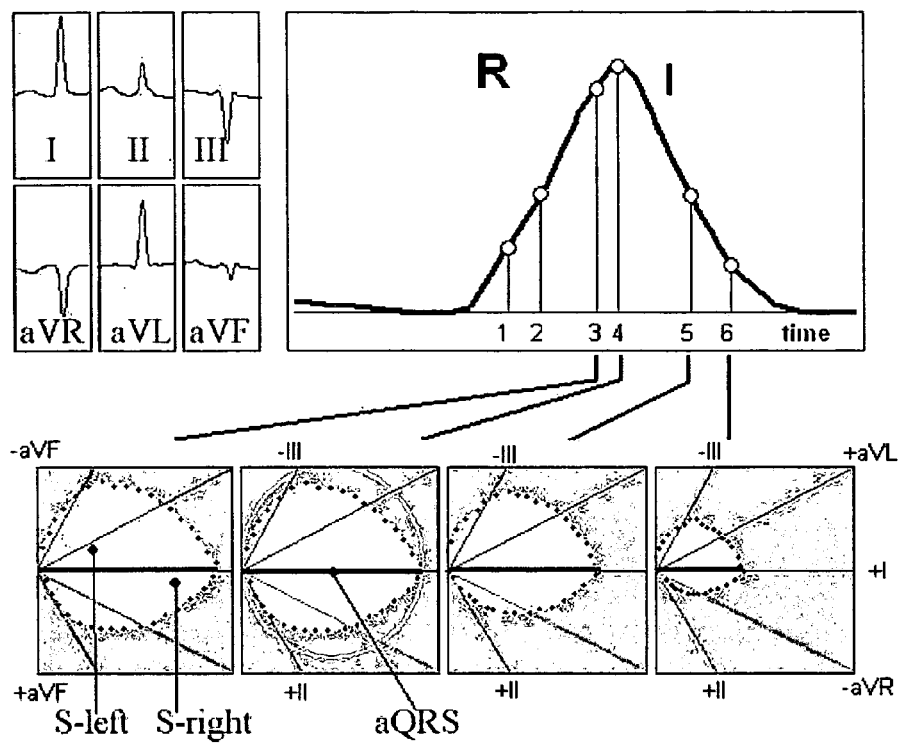
FIG. 10 illustrates electrical fluctuations and corresponding mapping of voltages during depolarization of a healthy heart.
Figure 11:
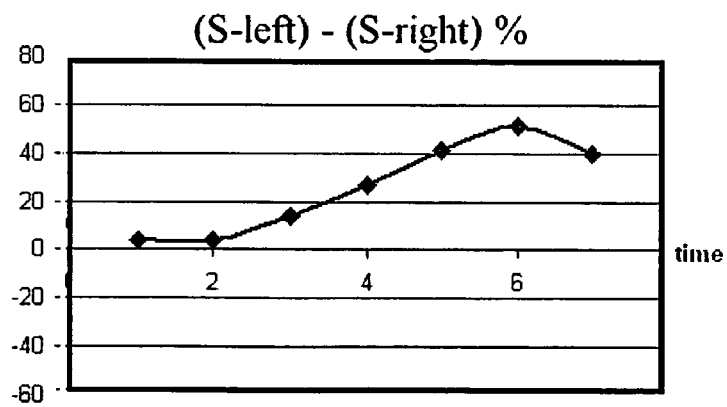
FIG. 11 illustrates the electrical relationship between the excitation of the left and right ventricles, of the healthy heart of FIG. 10.

FIG. 10 illustrates this ellipse evolution during depolarization of ventricles of a heart of a healthy man. The character of this evolution varies considerably at the very first signs of a myocardial infarction, when on the initial ECG still there are no changes. Similarly, for diagnostics of ventricle blockage, the large significance exhibits a change in an integral metric of electrical asymmetry of excitation of ventricles. This change is the difference between the square of the ellipse to the left of a maximum and to the right of a maximum, as shown in FIG. 11. Actually, new diagnostic information is obtained as to a synchronism of ventricle excitation.

Figure 12:
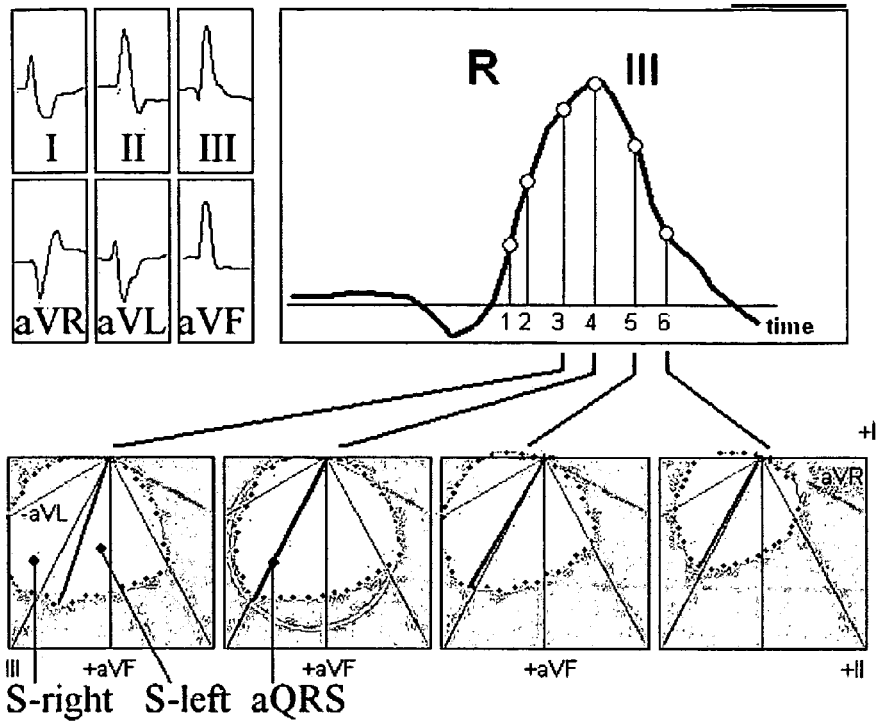
FIG. 12 illustrates electrical fluctuations and corresponding mapping of voltages during depolarization of a heart with pathological state.
Figure 13:
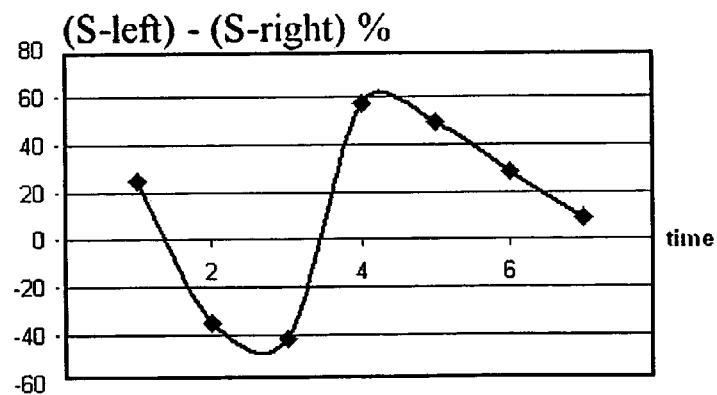
FIG. 13 illustrates the electrical relationship between the excitation of the left and right ventricles, of the heart of FIG. 12.

In FIG. 12, similar information for the heart of a man with a serious pathological state is illustrated. The considerable instability of the ellipse and entirely different character of electrical asymmetry of depolarization of ventricles as compared to FIGS. 10 and 11, are visible. The index of electrical asymmetry as shown in FIG. 13 has a high specificity.

Figure 14:
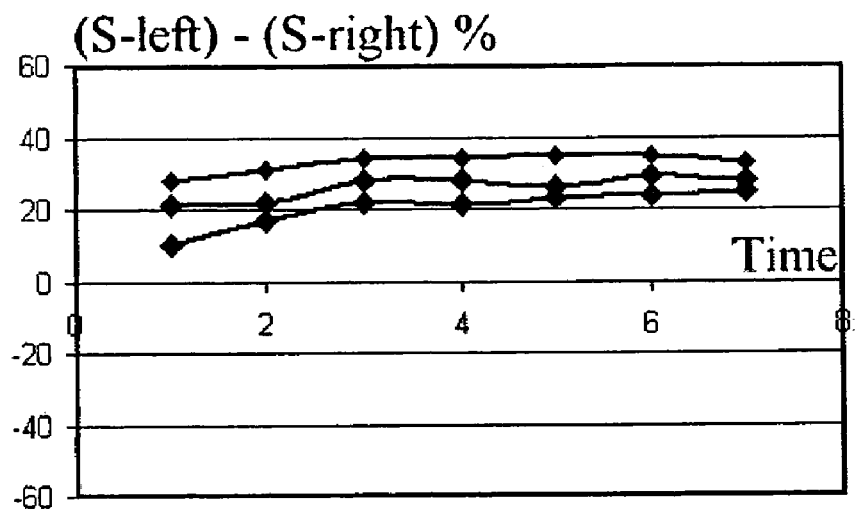
FIG. 14 illustrates consistency and electrical characteristics for the healthy heart of FIG. 10.
Figure 15:
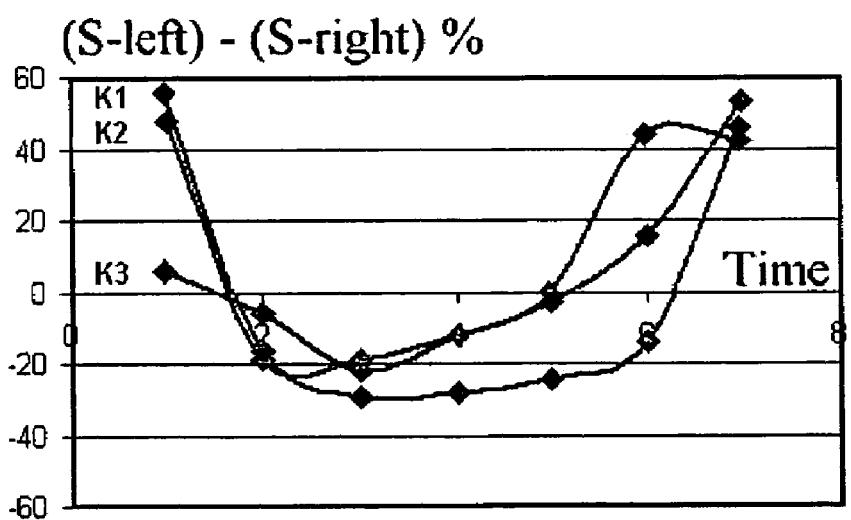
FIG. 15 illustrates the inconsistency and electrical characteristics for the heart of FIG. 12.

In FIG. 14, three sequential measurements of electrical asymmetry of ventricles for the patient with a normal heart are shown. And in FIG. 15, three measurements for the patient with the large deviations are illustrated. The axis of time in these measurements corresponds to an interval between a beginning and the termination of wave R.

The digital arrays of additional leads provide physical information, in that they mirror real electrical processes along a frontal surface of a body of a patient. In spite of the fact that the electrical voltages of additional leads are calculated values, they coincide with voltages, which can be actually measured on a surface of a body. The digital arrays of additional leads are not a result of computer interpretation of physical signals, as are signals in standard ECG leads. Because a very large number of these arrays can be obtained, amounting to approximately 90,000 values for a 1 second input of an ECG, a most exact and effective way of immediate observation of the array is a map. Such a map can be constructed according to the previously noted principle of localization or transposing on an epicardium of a computer generated three-dimensional model of a heart. The large sets of arrays are represented on a display screen by color coding according to number or value. Using known standards of statistical analysis, for example, green corresponding to a normal state, initial stages of pathological changes can correspond to yellow, and severe pathology can correspond to red.

Figure 16:
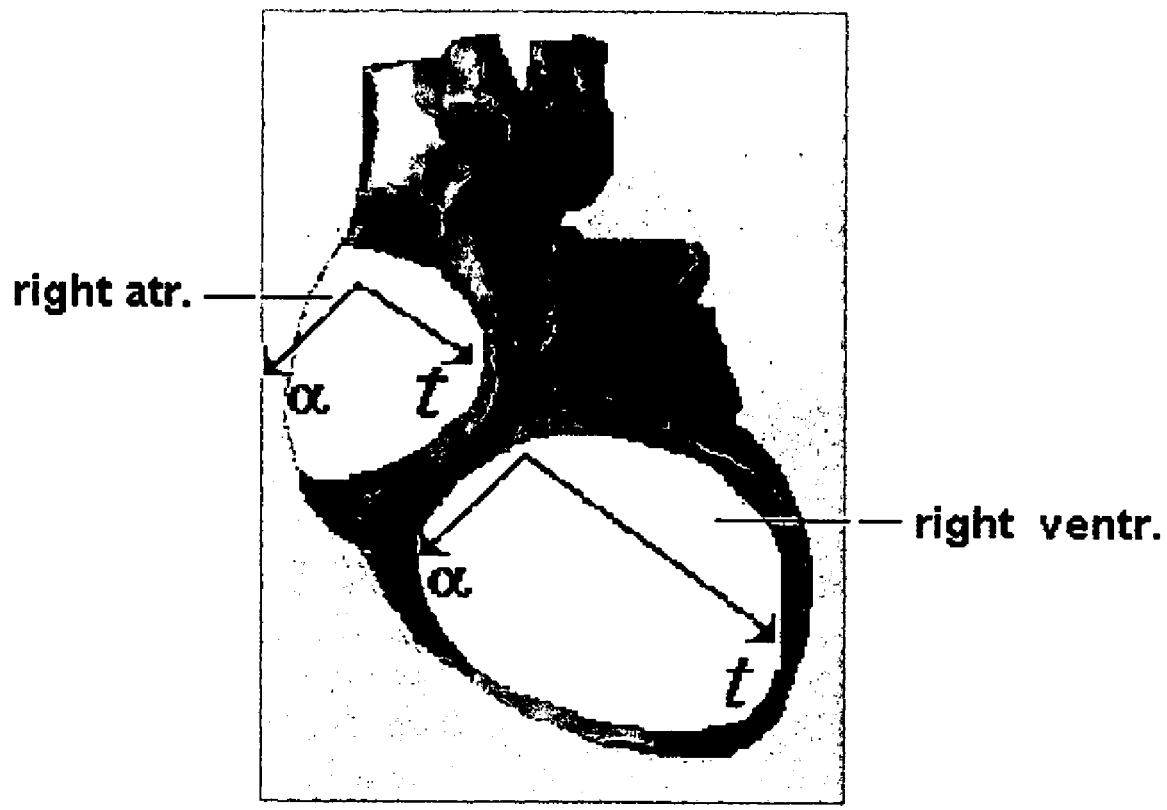
FIG. 16 illustrates the coordinate axes of a topological model on an anatomic portrait of the right side of a heart's epicardium.
Figure 17:
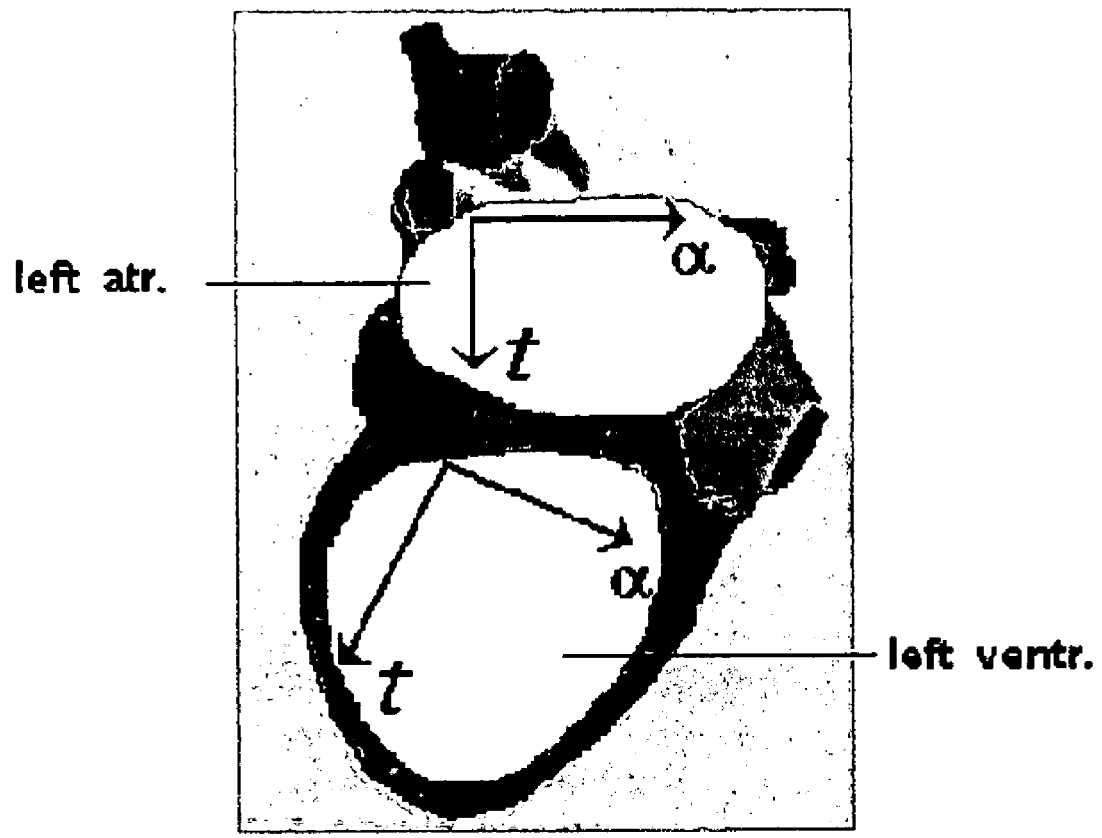
FIG. 17 illustrates the coordinate axes of a topological model on an anatomic portrait of the left side of a heart's epicardium.

The locations of points or rather, the locations of transposed values on a topological model are such, that the axis QRS approximately coincides with a projection of an inter ventricular septum. The angle $\alpha$ to the right from an axis QRS covers a surface of a right ventricle. The angle $\alpha$ to the left from an axis QRS covers a surface of a left ventricle. This is shown in FIGS. 16 and 17. There, a direction from the basis of the heart to its top corresponds to an axis of time. Similar relations exist for axes ($\alpha$, t) for atriums.

Figure 18:
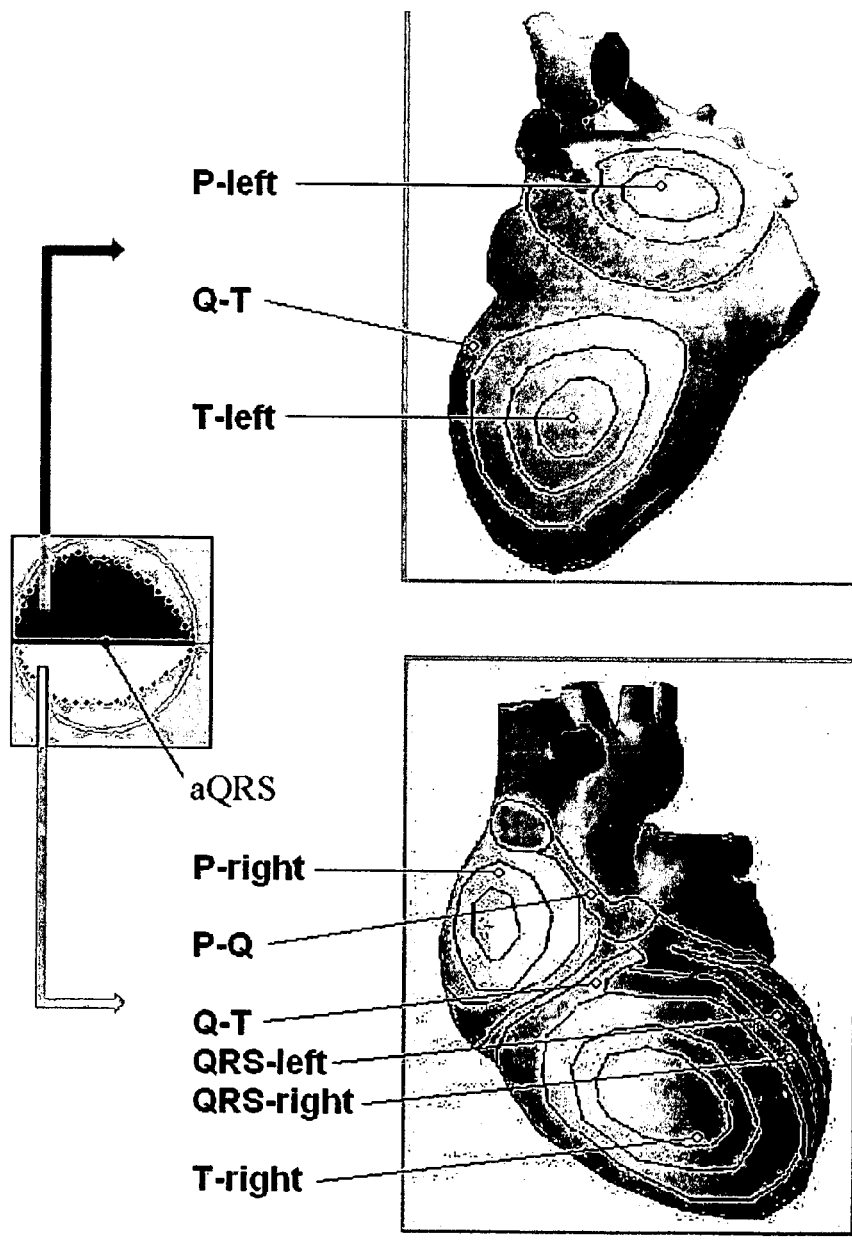
FIG. 18 is an anatomic portrait of a heart.

As a result, the anatomic portrait of a heart is obtained, which structure is represented in FIG. 18. The model maps not only information on topology and amplitudes of electrical excitation for two atriums and two ventricles, but also contains the indirect data of the dynamics of the PQRST complex (e.g. dynamics of intervals P-Q and Q-T). The character of the color-coding corresponds to standards, which for example can be as follows: green or light-blue color corresponds to normal, and red corresponds to large deviations.

All operations and calculations described herein relate to the process of depolarization of ventricles, i.e. to wave R. However, the same operations and calculations are applicable for waves P (depolarization of atriums) and T (repolarization of ventricles).

Further, it is possible to build separate anatomic portraits for each process of depolarization and repolarization, or graphically to combine them on one three-dimensional map according to localization of pathological changes. It will be appreciated by those skilled in the art that known techniques of computer imaging, graphing, and manipulation of digital arrays can be used, to provide specific representations of the methods and information described herein.

In a broad sense, the preferred embodiment method includes the following operations. On an initial ECG signal, a PQRST-complex is identified. At some predetermined interval, selected PQRST-complex electrical voltages of any two standard leads: I-III, either I-II, or II-III are measured and recorded or otherwise stored or captured.

Two base voltages U1 (t), U3 (t) are defined under the following formulas:

If leads I-III are selected:

$U1(t)=I, U3(t)=III.$

If leads I-II are selected:

$U1(t)=I, U3(t)=II-I.$

If leads II-III are selected:

$U1(t)=II-III, U3(t)=III.$

Next, the U1 (t), U3 (t) data is transformed to a digital array of values.

Then, the digital arrays of additional leads Ampl ($\alpha$, t) ($\alpha$—the angle in a six-axial coordinate system varies from −60 up to +120) are calculated under the following formulas:

If $\alpha$=−60 . . . 0, $Ampl(\alpha, t)=U1(t)-(1-(\alpha+60)/60)*(U1(t)+U3(t));$ If $\alpha$=0 . . . +60, $Ampl(\alpha, t)=U1(t)+(\alpha/60)*U3(t);$ If $\alpha$=+60 . . . +120, $Ampl(\alpha, t)=U3(t)+(1-(\alpha-60)/60)*U1(t);$ (* designates an operation of multiplying).

The number of such arrays for all practical purposes is defined by the increment of calculations on angle $\alpha$. For example, this number can be 180. The less increment for angle $\alpha$, the greater resolution of the resulting topological model.

For each stage of electrical excitation of a heart, namely for wave P, wave R and wave T, the direction of an axis of maximum excitation is defined with the arrays Ampl ($\alpha$, t). For this purpose, at a point tmax, which corresponds to the maximum amplitude of an appropriate wave, an angle $\beta$ is defined, at which the value Ampl ($\beta$, tmax) has a maximum value. The value divides the arrays Ampl ($\alpha$, t) into the left and right halves. If an angle $\alpha<\beta$, the array Ampl ($\alpha$, t) correlates with the left region of a heart. If $\alpha>\beta$, the array Ampl ($\alpha$, t) correlates with the right region of a heart. For each of the considered waves, three directions of maximum excitation are obtained: $\beta\_P$ for wave P, $\beta\_R$ for wave R, $\beta\_T$ for wave T.

The points of each array Ampl (a, t) are mapped onto an appropriate surface of an anatomic computer generated three-dimensional model of a heart according to the following conditions for coordinate axes (a, t): if a<b, such point is placed on the left region of heart (left atrium or left ventricle). If a>b, such point is placed on the right region of heart (right atrium or right ventricle). At any given value of a, the t axis extends from the basis of the three-dimensional heart model to an apex (FIGS. 16 and 17). The points of the array Ampl (a, t) are transposed on a surface of the appropriate region of the three-dimensional heart model evenly and uniformly, without skips and condensations.

Because the value $\beta$ varies during electrical excitation, all effects of the enlarged (abnormal) electrical asymmetry of the left and right regions of a heart are clearly visible on a topological model.

Figure 19:
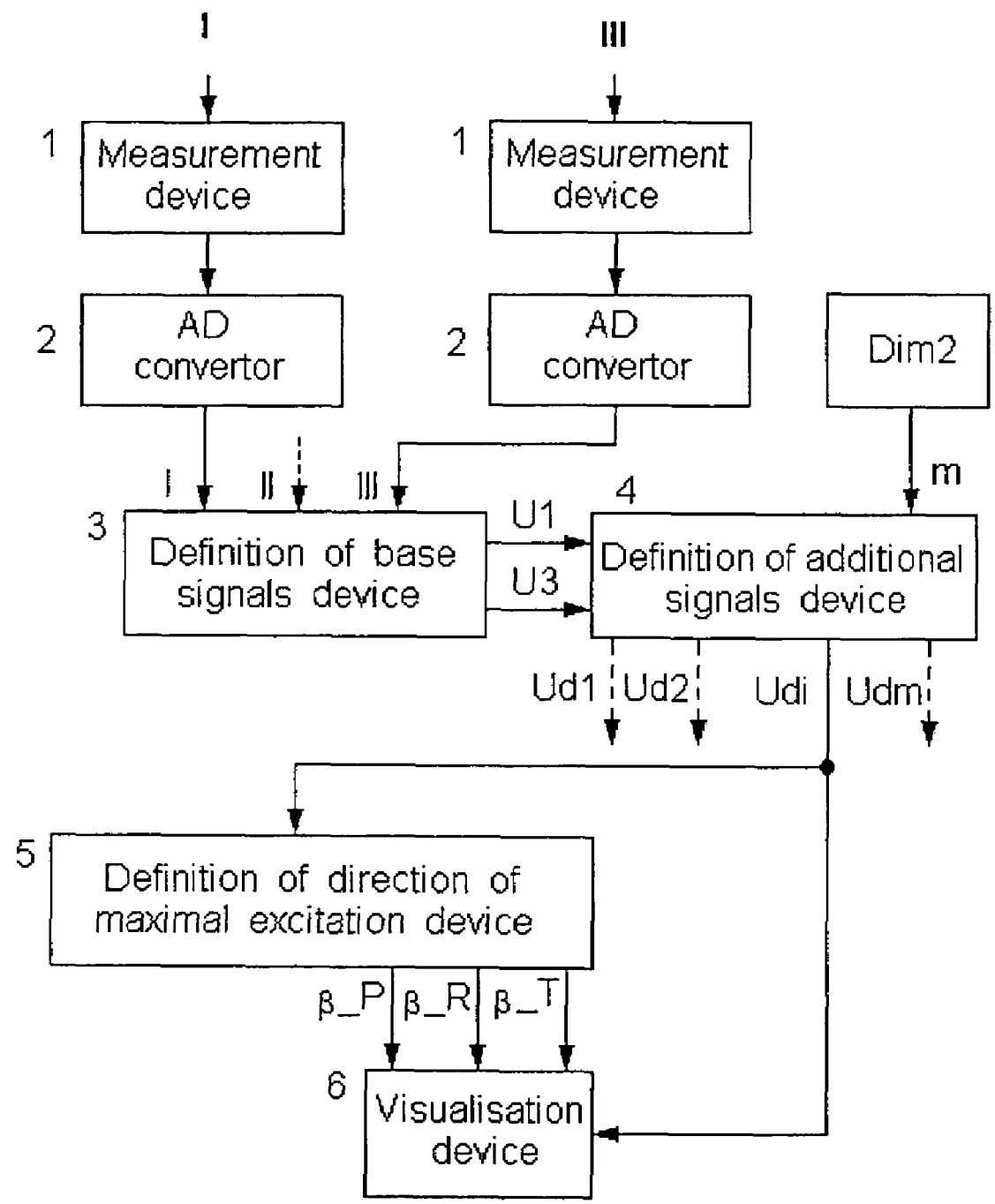
FIG. 19 is a flowchart for a preferred embodiment process in accordance with the present invention.

A flowchart corresponding to a preferred embodiment method is depicted in FIG. 19. Two lines of operations shown as blocks (1,2) transform electrical voltages of two standard leads (for purposes of example in FIG. 19, standard leads I and III are selected) in digital form. The output digital values of two indicated lines of signal processing are transmitted to inputs I and III of the block (3). The block (3) forms at any moment of time, two base signals U1 (t), U3 (t). The signals U1 (t), U3 (t) are transferred to an input of the block (4) which forms signals of additional leads Ud1 (t), . . . , Udm (t). The number of additional leads m (index of resolution of the analysis) is defined by a constant signal, which is transferred to an additional input of the block (4) from the block Dim2 and defines the step of the analysis on the value of an angle α of the coordinate system. The step of 30 degrees (m=6) corresponds to the least resolution, the value of a step of 1 degree (m=180) corresponds to the highest resolution. From an output of the block (4), arrays Udi (t), which number m is defined by a signal from the block Dim2, sequentially are transferred to the block (5) for further processing.

The arrays Ud1 (t), . . . , Udm (t) and three signals β_P, β_R, β_T from the block (5) are transferred to an input of the box (6). The arrays and signals define an axis of maximum excitation for processes of depolarization of atriums, depolarization of ventricles and repolarization of ventricles.

As a result of implementation of the noted processes, a new method is obtained, which enables building of an information model of electrical excitation of a heart in the form of an anatomic portrait of heart. The new model gives the exact information on type and localization of a pathological state. This new model can only be constructed using blocks 3, 4, and 5 in FIG. 19, as these blocks allow calculating a direction of an axis of maximum excitation and distribution of amplitudes on both sides from this axis.

The anatomic portrait of a heart as provided herein qualitatively changes the review, evaluation, and assessment of an ECG by an investigator or physician. The analysis of differential signs of an ECG enables one to see an entire picture of state changes as a whole and at once. Thus the information portrait as compared to graphs of potentials, provides not only anatomic topology of changes, but also information on the dynamics of the operation of a heart. This enables another important advantage, in that color can be used to characterize deviance from a normal state, instead of evaluating the value of a potential.

The secondary space of fluctuation featured in the given method is considerably steadier in matching with space of standard differential signs of ECG analysis. It allows creating a very reliable automatic interpreter of heart portraits considerably exceeding the reliability of existing automatic diagnosis interpreters of an ECG signal.

Figure 20:
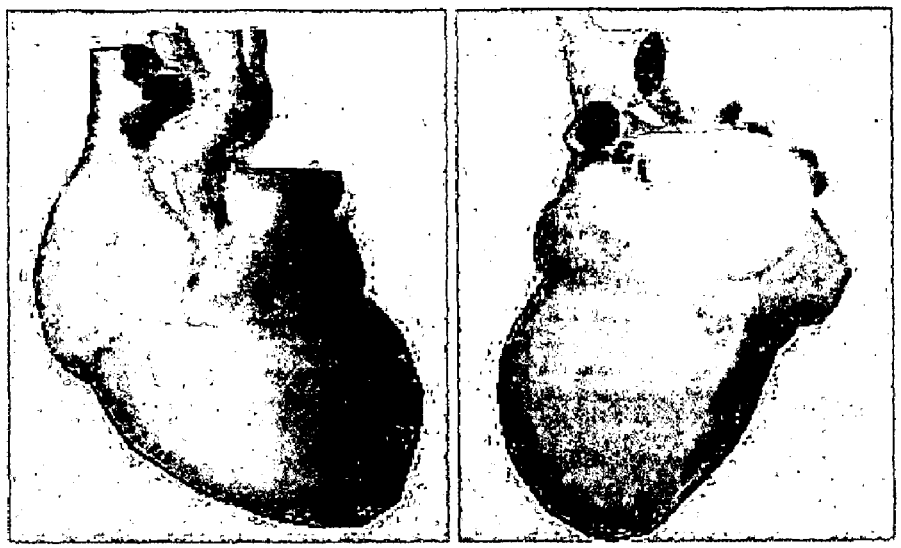
FIG. 20 is a portrait of healthy heart.
Figure 21:
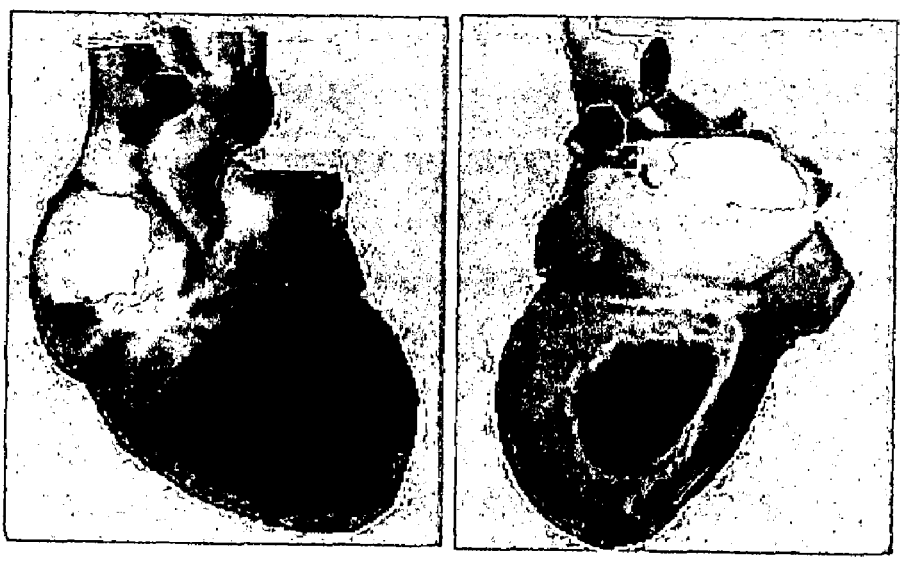
FIG. 21 is a portrait of heart with pathological state.

Examples of images obtained using the preferred embodiment method are provided in FIG. 20 and FIG. 21. For these evaluations, the time of input of an ECG-signal was 30 seconds. In FIG. 20 the heart portrait of the previously mentioned healthy person is represented in two projections—right-side view, and a left-side view. In FIG. 21 a portrait of a heart with a pathological state is depicted. The obtained portraits have very high sensitivity and specificity, and also demonstrate very high repeatability.

Figure 22:
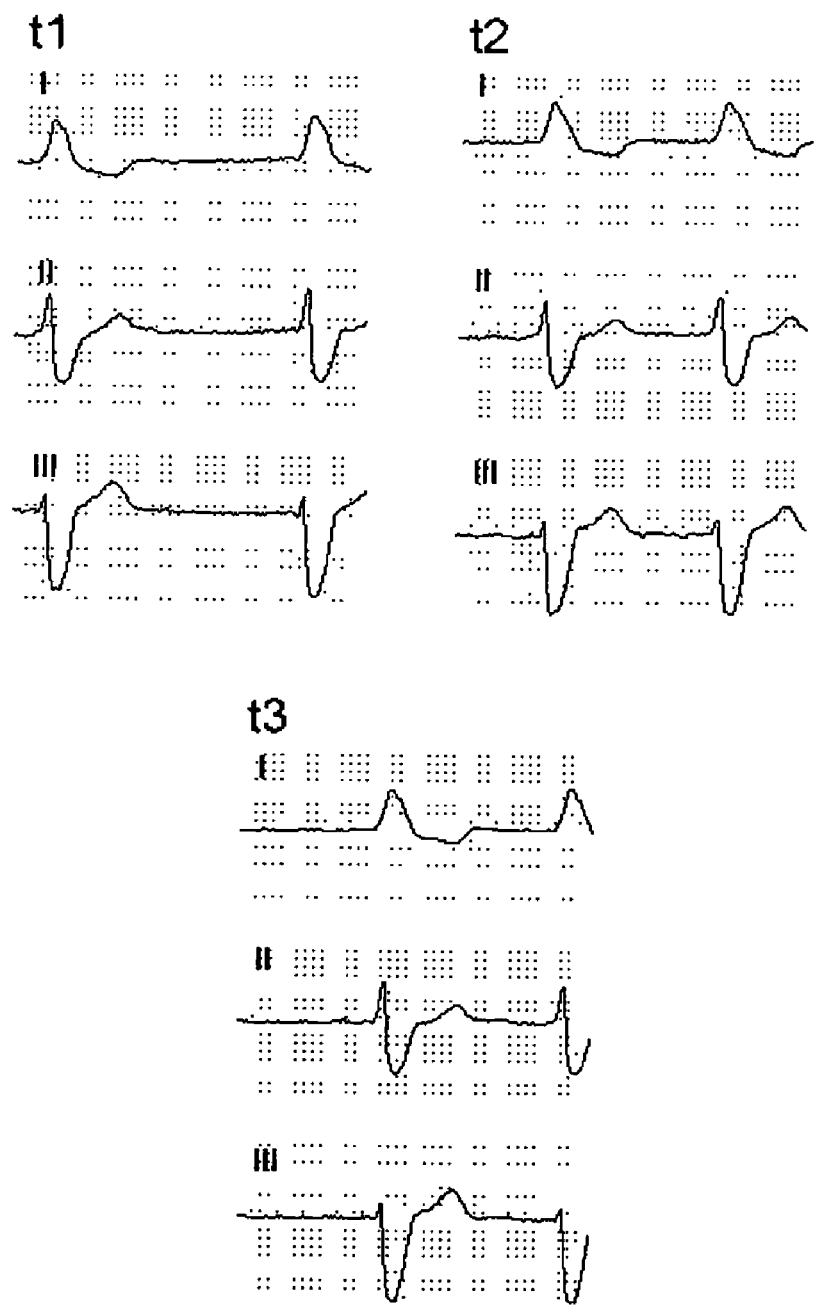
FIG. 22 is an ECG signal evolution for a hidden ischemic disease.
Figure 23:
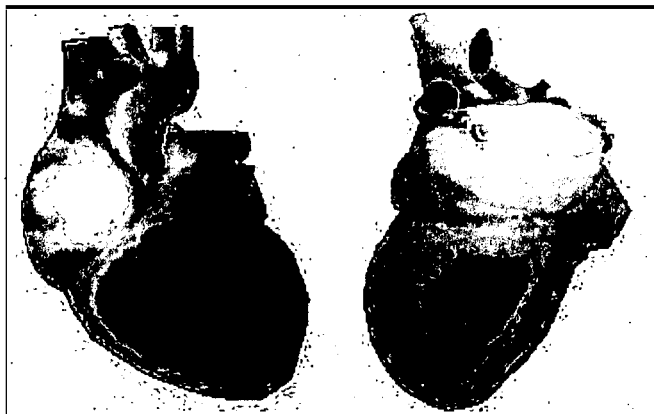
FIG. 23 is heart portrait's evolution for the hidden ischemic disease.
Figure 23:
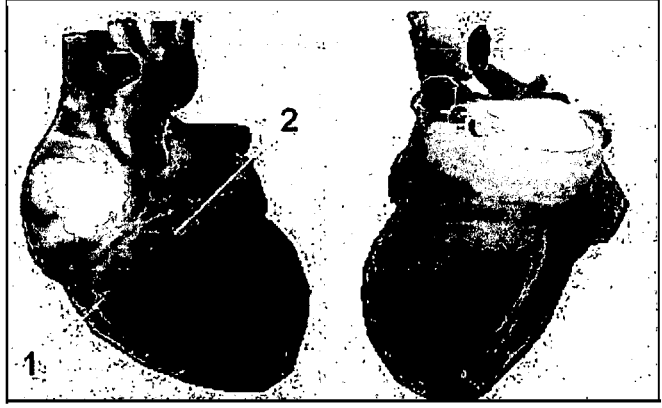
Figure 23:
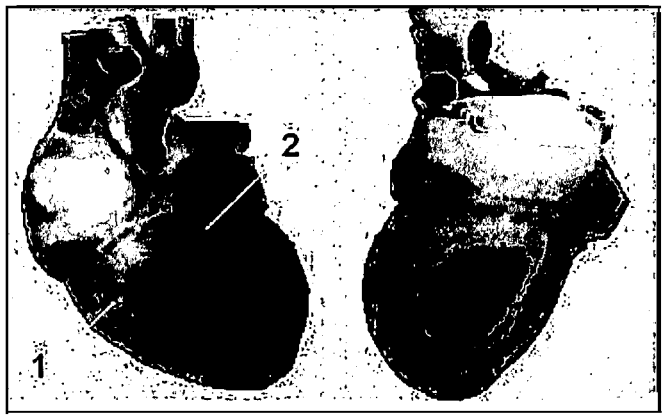

Deficiencies in conventional ECG analysis are shown in the following examples depicted in FIGS. 22 and 23. Three examinations t1, t2, t3 were obtained during treatment of a patient in a hospital with an interval of several days. The diagnosis was ischemic disease of heart, and atherosclerosis of coronary arteries. In FIG. 23, the entry of standard ECG leads I, II, III were transposed on appropriate portraits of the heart. From a review of an ECG-signal, it is difficult to see significant changes in these three examinations as can be seen in FIG. 22. As shown in FIG. 23, the tendency of decrease of deviations in a right ventricle is clearly visible with heart portraits constructed in accordance with the preferred embodiment of the present invention. The green color was partially restored in the field of 2, and the intensity of red color in "ellipse" 1 decreases noticeably and monotonically. These changes are reliable signs of slow improvement of a state, which is not visible with traditional ECG analysis. The given example indicates the unique possibilities of the present invention, and particularly in the task of precise and operative observation of heart responses to executable therapy. These responses are very important with regard to the choice and adjustment of tactics of medical treatment.

Figure 24:
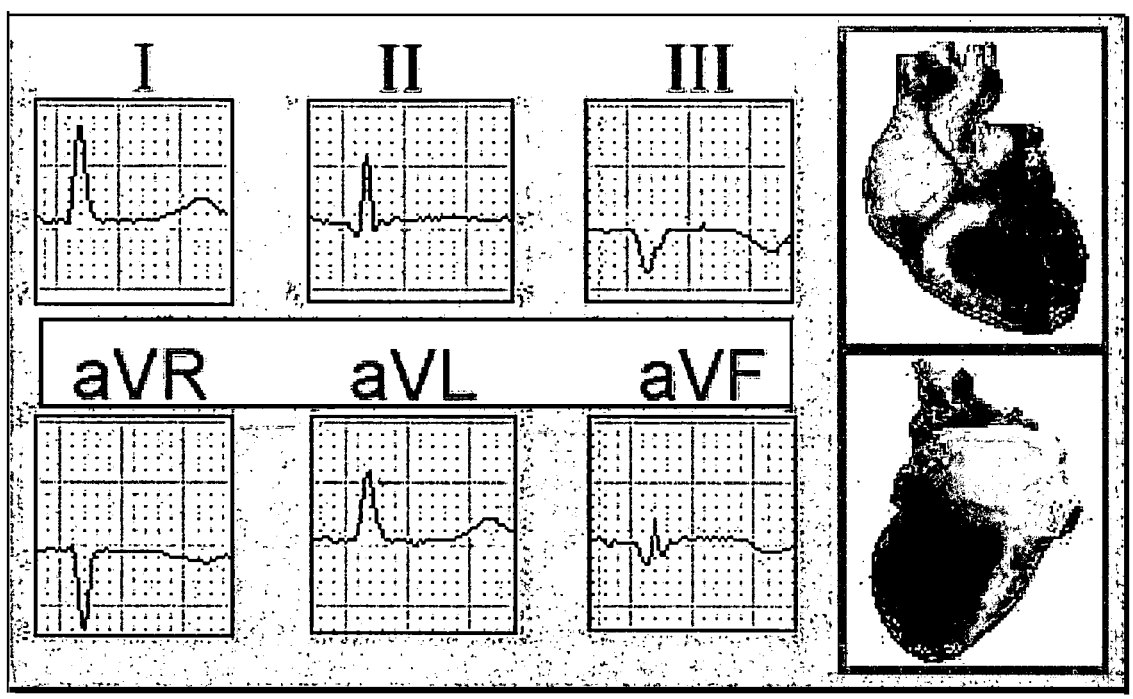
FIG. 24 is a heart portrait for a mild myocardial infarction.

The sensitivity of the preferred embodiment method in detection of pathologies which would otherwise remain undetected, is further illustrated by diagnostics of a small local myocardial infarction in FIG. 24. The initial ECG signal does not contain any essential signs of cicatrical changes. The electrocardiogram of terminal leads I through aVF in many cases corresponds to a normal state. However upon review of the heart portrait constructed to the present invention, a pathological view (red in the field of the left and right ventricles with prevalence in the side of a left ventricle) is clearly provided. The investigator or physician in this case, can readily conclude that signs of cicatrical changes of lower localization, suggest that complete clinical examination is necessary.

In accordance with the present invention, various preferred embodiment systems are also provided. The systems enable or work in conjunction with other components to enable an investigator or physician to readily assess the state of a heart. A preferred embodiment system generally comprises a processor or computer having inputs and outputs for receiving and providing signals or information and one or more storage devices for storing data or information. The processor is adapted or otherwise programmed to perform the various calculations and algorithms described herein. The noted inputs are preferably adapted to receive standard leads from a conventional 6 lead or 12 lead electrocardiogram. The noted storage devices can be in the form of readable media such as a hard drive or disk, or can be in the form of memory such as RAM. The storage device can also be in the form of nearly any computer-readable medium. The term "computer-readable medium" as used herein includes any type of computer memory or storage device such as but not limited to floppy disks, hard disks, CD-ROMS, Flash ROMS, nonvolatile ROM, and RAM. The system also preferably includes a display device for displaying or presenting information obtained or generated by the processor. The display device can for example be in the form of a monitor or other similar component, or can also be in the form of a printer or other image-forming device. The various devices or components are in communication with one another via a wired or wireless communication path, such as a network, serial or parallel port, or any other suitable means of communication. The preferred embodiment system may include a keyboard, keypad, pointing device or other types of input controls to operate the processor device. The input control may also include a measurement device and/or a communication port by which other data may be received.

Although not wishing to be limited to any specific system, a particularly preferred system in accordance with the present invention is a commercially available laptop computer that is programmed to execute the calculations and algorithms described herein. A standard electrocardiogram module including all limb electrodes (e.g. two ankle electrodes and two wrist electrodes), appropriate cabling, and sensor inputs is used in conjunction with an appropriately configured laptop computer. In use, the limb electrodes are attached to a subject, cabling connected between the electrodes and the laptop computer (or signal processor component placed between the computer and the electrodes), and signals measured and stored by the laptop from the electrodes for a predetermined period of time. The laptop is configured to calculate the standard leads and to further determine the additional leads from any two standard leads. Further processing is performed by the laptop according to the methods described herein, to ultimately provide an array of values that are mapped onto a three dimensional model of a heart and the resulting mapped model is shown on the laptop display. Known algorithms can be used for generation of a three-dimensional model of a heart.

The present invention also provides computer-readable media having computer-executable instructions for performing the methods described herein. Specifically, in one version, a preferred embodiment computer-readable media contains computer executable instructions for performing a method of assessing the state of a heart using limb electrodes. The method involves defining two arrays of base voltages from two standard leads determined from the limb electrodes. After appropriate selection of a time interval, additional leads are calculated from the arrays of base voltages defined and the time interval selected. The calculated leads can be reviewed to assess the state of the subject's heart. In a further preferred embodiment, the method is performed as noted above and then further defines an axis of maximum excitation from the additional leads and forms sets of arrays of valves that provide information relating to the state of the heart of the subject. In a still further preferred embodiment, the method performed by the computer-executable instructions retained on the computer-readable media includes mapping the sets of arrays of values onto a model of a heart.

The following is an example of calculating or otherwise determining additional leads. A PQRST-complex is selected. Referring to FIG. 7, slipping contact i9 (the contact is identified by a current "i9", which flows through the contact) is placed in the right most position, i.e. the slipping contact will appear connected with a point F. At this position of contact there corresponds in a six-axial coordinate system an angle −60, and designed parameter=0/(R1+R2)=0. A source E1 is submitted as a voltage from the first lead (which is measured in lead I in this instant, and which is designated U1), and as a source E3—voltage U3 from lead III in the same instant. Then, the measuring instrument connected to a resistance r-aVL, will show a voltage peer U3. If not measuring this voltage, it can be calculated under Kirhgoff's laws by the formulas:

If α=−60 . . . 0, then $$\lambda = (\alpha+60)/60 \tag{f1}$$

(f2) Ampl (α, t)=U1 (t)−(1−λ)*(U1 (t)+U3 (t)); is real, at "lambda"=0 Ampl (a, t)=U1 (t)−U1 (t)−U3 (t)=−U3 (t). And so, the change of a relative resistance R1/(R1+R2) and parameter "lambda" in a six-axial coordinate system are absolutely identical.

Referring to FIG. 7, moving slipping contact slightly to the left so that the ratio of an electrical resistance R1, which is more to the right of slipping contact, to a common resistance between points F and R, becomes peer 1, i.e. R1/(R1+R2)=1/60~0,017. It corresponds in a six-axial coordinate system to an angle −59, at which "lambda"=(−59+60)/60=1/60~0.017.

Again a source E1 is submitted as a voltage from the first lead (which is measured in lead I in this instant, and which is designated U1), and as a source E3—voltage U3 from lead III in the same instant. Then, the measuring instrument connected to a resistance r-aVL, will show a voltage peer Ampl (a, t)=U1 (t)−(1−0.017)*(U1 (t)+U3 (t))=0.017U1 (t)−0.993U3 (t).

Referring further to FIG. 7, moving slipping contact to the left for one more step so that the ratio of an electrical resistance R1, which is to the right of slipping contact, to a common resistance between points F and R, becomes peer 2/60, i.e. R1/(R1+R2)=2/60~0.035. It corresponds in a six-axial coordinate system to an angle −58, at which "lambda"=(−59+60)/60=1/60~0.035. And so on. Through such 60 steps R1/(R1+R2)=60/60~1.0, "lambda"=(0+60)/60=60/60~1.0, and Ampl (a, t)=U1 (t)−(1−1.0)*(U1 (t)+U3 (t))=U1 (t).

Voltage in the first 60 points thus will be obtained.

In accordance with a preferred embodiment, instead of displacing slipping contact i9 60 times (through an angle of 1 degree), an equivalent microprocessor calculation is used.

Further, having placed slipping contact i12 (contact is identified by a current, which flows through it (FIG. 7)) in the right most position, i.e. the slipping contact will be connected with a point L. To this position of contact there corresponds in a six-axial coordinate system an angle 0, and designed parameter "lambda"=0/(R1+R2)=0, since for this slipping contact the counting goes from the right end of a resistance between points R and F. A source E1 is submitted as a voltage from the first lead (which is measured in lead I in this instant, and which is designated U1), and as a source E3—voltage U3 from lead III in the same instant. Then, the measuring instrument connected to a resistance r-aVR, will show a voltage peer U1. If not measuring this voltage, it can be calculated under Kirhgoff's laws under the formulas:

$$\lambda = \alpha/60 \tag{f3}$$

$$\text{Ampl } (\alpha, t) = U1(t) + \lambda * U3(t) \tag{f4}$$

When 60 shifts of slipping contact i12 occur, 60 voltages will result, and the latter (at an angle=60) will be equal to U1+U3, i.e. and is precisely equal to a voltage on lead II (lead II is a voltage between points R and F).

Similar operations with slipping contact i15 produce the last 60 points. In result, for the first instant on the initial voltages U1, U3 180 "additional leads" can be obtained.

The described procedures are repeated for the second temporary point of the complex PQRST etc. In total, the number of interrogations of two initial leads I (i.e. U1) and III (i.e. U3) will turn out 180*N of numbers, where N—the number of time slices of only TWO basic leads I (i.e. U1) and III (i.e. U3).

The foregoing description is, at present, considered to be the preferred embodiments of the present invention. However, it is contemplated that various changes and modifications apparent to those skilled in the art, may be made without departing from the present invention. Therefore, the foregoing description is intended to cover all such changes and modifications encompassed within the spirit and scope of the present invention, including all equivalent aspects.

The invention claimed is:

1. A method of assessing the state of a heart, the method comprising:
   placing limb electrodes on a body of a patient for which assessment of the state of the heart is to be made;
   selecting two standard leads from the limb electrodes;
   measuring electrical voltages in each selected standard lead to define two arrays of base voltages;

selecting a time interval;

calculating additional leads as a function of an angular position from the arrays of base voltages defined and the time interval selected to generate a curve of ellipse of electrical voltages of additional leads in each point of the selected time interval; and reviewing change over time of the ellipse of electrical voltages of the additional leads over the selected time interval to assess the state of the heart of the patient, the reviewing comprising defining in each moment of time of myocardium depolarization and repolarization an asymmetry of the ellipse of electrical voltages as a difference between a square of an area of the ellipse one side of a spatial axis of maximum excitation and a square of an area of the ellipse on the other side of the spatial axis of maximum excitation.

* * * * *